(12) United States Patent
Schafer et al.

(10) Patent No.: US 12,306,364 B2
(45) Date of Patent: May 20, 2025

(54) QUALITY ASSURANCE DEVICES AND METHODS TO ENSURE PROPER ULTRASOUND EXPOSURE

(71) Applicant: BrainSonix Corporation, Sherman Oaks, CA (US)

(72) Inventors: Mark E. Schafer, Ambler, PA (US); Samantha F. Schafer, Ambler, PA (US); James M. Gessert, Longmont, CO (US)

(73) Assignee: BrainSonix Corporation, Sherman Oaks, CA (US)

( * ) Notice: Subject to any disclaimer, the term of this patent is extended or adjusted under 35 U.S.C. 154(b) by 607 days.

(21) Appl. No.: 17/686,649

(22) Filed: Mar. 4, 2022

(65) Prior Publication Data
US 2022/0283328 A1 Sep. 8, 2022

Related U.S. Application Data

(60) Provisional application No. 63/157,248, filed on Mar. 5, 2021.

(51) Int. Cl.
*G01V 1/18* (2006.01)
*A61N 7/00* (2006.01)
*G01K 1/02* (2021.01)

(52) U.S. Cl.
CPC .............. *G01V 1/186* (2013.01); *A61N 7/00* (2013.01); *G01K 1/02* (2013.01)

(58) Field of Classification Search
CPC ............. G01V 1/186; A61N 7/00; G01K 1/02
See application file for complete search history.

(56) References Cited

U.S. PATENT DOCUMENTS

| 2013/0289593 A1* | 10/2013 | Hall | A61N 7/02 264/109 |
| 2017/0254887 A1* | 9/2017 | Sapozhnikov | G01S 15/8918 |
| 2020/0033187 A1* | 1/2020 | Ivanytskyy | G10K 11/006 |

FOREIGN PATENT DOCUMENTS

| FR | 2728754 A1 * | 6/1996 | B06B 1/0688 |
| WO | WO-2016190226 A1 * | 12/2016 | A61B 5/0095 |

OTHER PUBLICATIONS

European Patent Office, International Preliminary Report on Patentability and Written Opinion issued in International Patent Application No. PCT/US2022/018849 on Aug. 29, 2023; 6 pages.

(Continued)

*Primary Examiner* — Isam A Alsomiri
*Assistant Examiner* — Abdallah Abulaban
(74) *Attorney, Agent, or Firm* — Thompson Hine LLP

(57) ABSTRACT

Calibration or quality assurance devices and methods that ensure proper ultrasound exposure. An apparatus for calibrating an ultrasound transducer is provided. The apparatus includes a hydrophone assembly having a layer containing a solid material and a hydrophone element embedded in the solid material of the layer. A method of calibrating a therapeutic ultrasound system including an ultrasound transducer and system electronics is also provided. The method may include connecting the ultrasound transducer to an electronics module, separately connecting the system electronics to the electronics module, driving the ultrasound transducer at a given frequency to emit an ultrasound beam, sensing the ultrasound beam with a hydrophone element, and measuring a signal that is output from the hydrophone element.

19 Claims, 4 Drawing Sheets

(56) References Cited

OTHER PUBLICATIONS

European Patent Office, International Search Report and Written Opinion issued in International Patent Application No. PCT/US2022/018849 on Jun. 1, 2022, 10 pages.
European Patent Office; Communication pursuant to Article 94(3) EPC issued in European Patent Application No. 22713795.7 on Mar. 12, 2025; 6 pages.

* cited by examiner

QUALITY ASSURANCE DEVICES AND METHODS TO ENSURE PROPER ULTRASOUND EXPOSURE

CROSS-REFERENCE TO RELATED APPLICATIONS

This application claims the benefit of U.S. Provisional Application No. 63/157,248, filed Mar. 5, 2021, which is hereby incorporated by reference herein in its entirety.

TECHNICAL FIELD

The technical field relates to ultrasonics and focused ultrasound treatment of tissue using energy levels that do not cause damage such as heating or cavitation, and in particular to calibration or quality assurance devices and methods that ensure proper ultrasound exposure.

BACKGROUND

When treating tissue with ultrasound, the treatment should be conducted with the intended level of ultrasound energy. If the energy level is too low, the treatment may be ineffective. If the energy level is too high, the treatment may cause unintended negative biological effects. Consistency ensures that neither overtreatment nor undertreatment occur.

The ultrasound treatment system includes a system that can produce the necessary electrical drive signals; a transducer which converts those electrical signals into an ultrasound (mechanical) wave that is then transmitted into tissue; and a connection, typically a cable, that interconnects the drive system and the transducer. The transducer may have one or more electro-acoustic conversion devices within it, typically but not exclusively piezoelectric ceramic, composite, or single crystal elements. There are other portions of the overall treatment system, such as positioning, guidance, etc.

When the ultrasound treatment system is first delivered, installed, or set up at the treatment facility (e.g., hospital, clinic, physician's office), it is presumed to be in complete working order. This is usually confirmed by personnel familiar with the equipment, typically the installation service personnel of the company that manufactured the system. At that point, the acoustical output characteristics of the system are known. The goal then is to ensure that the output remains at that known level so that proper treatments are provided. The acoustic output relative to that initial condition is an indicator of a change in the condition of the system, and potentially a source of incorrect treatment.

There are potential causes of incorrect or improper treatment, principally a change in the efficiency, internal connectivity, focusing, or geometry of the transmitting ultrasound transducer; a change in the electronic system which electrically drives the transducer; or a change in the connection between the electronic system and the transmitting transducer.

The transmitting transducer is subject to aging after repeated use, especially with high drive levels which may be used for such treatment. More commonly, the transducer is subject to being accidentally dropped or mishandled in a way that affects the output of the transducer but does not cause any damage that might be assessed through visual inspection. For instance, a delamination of the internal structures would affect the acoustic output but would not be detectable by visual inspection. Similarly, a broken connection internal to the transducer can occur that would be undetectable.

The electronic system that drives the transducer may be subject to degradation of components, such as drive circuit transistors or feedback resistors, that could cause a change in the transmit voltage, either increasing or decreasing it. In either case, the treatment of tissue would not be as expected.

The cable or other type of connection between the electronic system and the transducer is also subject to hidden damage, for instance, if it were to be run over by the wheels of an equipment cart. This type of damage is not readily visible but can negatively affect the output performance of the entire system.

These issues may arise at the location, i.e. physician's office, hospital, clinic, or other health care facility, at which the treatment is to occur. The personnel who may be administering the treatment often are not technically qualified in the requisite engineering skills to perform a proper evaluation of the output of the ultrasound system. The treatment should be checked just prior to the actual administration of the ultrasound to ensure that the system is performing repeatably and within the expected or necessary clinical limits, both higher and lower than the intended level.

Further, for clinical research studies, the treatment should be consistent over the duration of the entire study, which can involve months or years. If the ultrasound system degrades with time, it may be that subjects who are treated at the end of the clinical trial do not receive the same treatment as those at the start of the trial, which may invalidate the entire trial.

Conventional systems exist to provide a simple, quantitative means to provide repeatability information with regard to the ultrasound delivered to the tissue. Such conventional systems are either very qualitative and inconsistent, are difficult for non-technical personnel to operate, or are specifically designed for a single system and not universally applicable.

Thus, there is a need for a simple-to-use, yet technically sophisticated, system or device to evaluate the ultrasound output consistency of an ultrasound treatment system. The device should check both the transmitter electronics, as well as the ultrasound transducer. At the same time, the device must be simple enough to be reliably operated by non-technical personnel, e.g. nurses, physician, medical technicians. The device should also be portable to be used at the treatment facility, and specifically nearby to MRI systems, which preclude magnetic materials or conductive loops within the MM room.

SUMMARY

In an embodiment, an apparatus for calibrating an ultrasound transducer is provided. The apparatus comprises a hydrophone assembly including a layer comprising a solid material and a hydrophone element embedded in the solid material of the layer.

In an embodiment, a method of calibrating a therapeutic ultrasound system including an ultrasound transducer and system electronics is provided. The method comprises connecting the ultrasound transducer to an electronics module, separately connecting the system electronics to the electronics module, driving the ultrasound transducer at a given frequency to emit an ultrasound beam, sensing the ultrasound beam with a hydrophone element, and measuring a signal that is output from the hydrophone element.

DETAILED DESCRIPTION

The embodiments of the invention described herein may permit rapid testing of ultrasound output, at the Point of Care, without technical (engineering) skills or large quantities of water. The embodiment of the invention described herein may provide information on the ultrasound output, the transducer electrical properties, and the electrical drive signal, in a manner that is highly repeatable. Absolute calibration is not required, as the relevant clinical issue is the change in output relative to that at the time of the initial installation. The embodiments of the invention described herein may also provide a measurement relative to the pressure amplitude of the ultrasound wave, in a manner that does not require a water tank.

Figure 1:
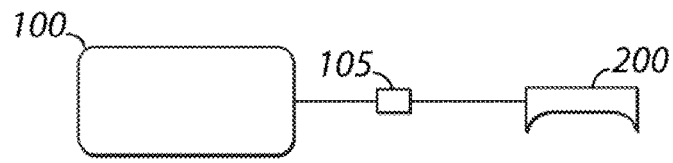
FIG. 1 is a schematic representation of an ultrasound treatment system in accordance with embodiments of the invention.

With reference to FIG. 1 and in accordance with embodiments of the invention, a system 100 may be configured to produce the electrical drive signals that a transducer 200 can convert into an ultrasound (mechanical) wave that is subsequently transmitted into tissue. The system 100 includes an electrical conductor (cable) that has an interconnect 105 providing a connection for connecting and disconnecting the system 100 to the transducer 200. In use, the system 100 and transducer 200 are connected via the interconnect 105. The cable can be a single coaxial element, such as RG-58, or a multi-conductor cable, depending upon the number of elements in the transducer 200. For ease of explanation, it may be assumed that transducer 200 is a single element, circular, spherically focused transducer, and that the cable is a single RG-58. The interconnect 105 may be a male/female pair of BNC connectors, but other connector types are possible. In use, the transducer 200 is positioned so that the focal zone is appropriately aimed at the tissue region to be treated, and the system 100 is turned on to apply an electrical signal, through the cable, to the transducer 200 so that it properly treats the tissue.

The connection between system 100 and transducer 200 may be separated, and reconnected, at interconnect 105. Typically, separation involves disconnection of a male/female pair of BNC connectors, but other forms of connection/disconnection are possible. If transducer 200 is comprised of multiple elements driven by multiple channels of electrical drive from system 100, the system 100 may be configured to control each channel of the electrical drive and each element of the multiple-element transducer.

Figure 2:
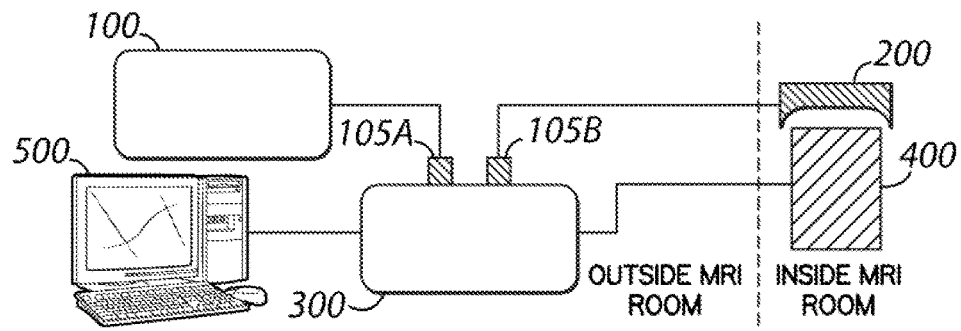
FIG. 2 is a schematic representation of an ultrasound treatment system in accordance with embodiments of the invention.

With reference to FIG. 2 and in accordance with embodiments of the invention, a system includes an electronics module 300, a hydrophone assembly 400, and a computer 500. The system may be used to test the system 100 and transducer 200 of FIG. 1. The interconnection between the system 100 and the transducer 200 is reconnected to the electronics module 300 by connectors 105A and 105B of the interconnect 105. One of the connections may be made between the system 100 and the electronics module 300 via connector 105A. Another of the connections may be made between the electronics module 300 and the transducer 200 using connector 105B. Thus, the electronics module 300 is electrically interposed between the system 100 and the transducer 200. In addition, the transducer 200 is acoustically coupled, as explained below, to the hydrophone assembly 400. The ultrasonic output waves from the transducer 200 are directed into the hydrophone assembly 400. The computer 500 is connected to electronics module 300 and provides control via software run on the computer 500. The computer 500 may be separate as illustrated, or may alternatively be incorporated into or with the electronics module 300. The electronics module 300 may also be operated by a microcontroller rather than a computer or microcomputer, depending upon the complexity of the user interface, complexity of the recording of test data, etc. If separate, the connection between the computer 500 and the electronics module 300 may be any of a number of connections, such as USB, Ethernet, RS-232, etc. The connection between the computer 500 and the electronics module 300 may supply operating power to the electronics module 300, for instance using a USB connection which affords power at 5 volts and different current levels depending upon the type of USB used. The electronics module 300 may also have a separate power supply source, such as from a wall transformer, battery (rechargeable or replaceable), etc.

The software running on the computer 500 may control the action of the electronics module 300, under the direction of an operator interfacing with the computer 500, in which instance the operator may utilize a User Interface (UI) suitable to the task. The exact nature of the UI may take any of a number of formats.

Figure 3:
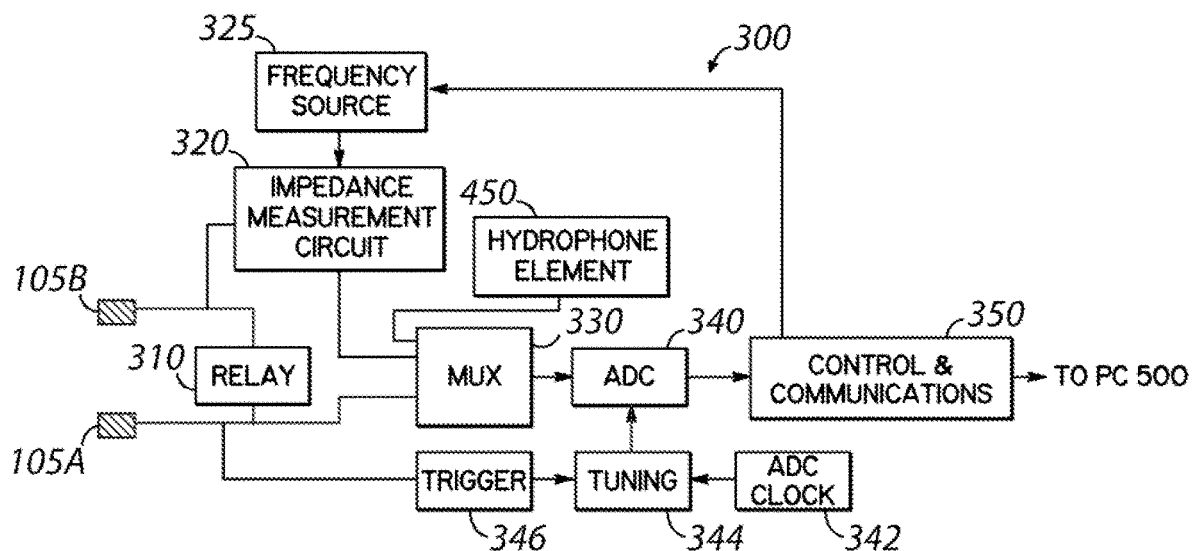
FIG. 3 is a schematic representation of an electronics module in accordance with embodiments of the invention.

FIG. 3 is a schematic representation of elements of the electronics module 300. The electrical drive signal from system 100 comes in via connector 105A. This signal goes to a relay 310 and also to a trigger circuit 346. The relay 310 is used to either electrically connect or isolate the electronics module 300 and the transducer 200. When isolated, the electrical drive signal can be evaluated independently of the transducer 200. Similarly, in the isolated state, the transducer 200 can be evaluated for its electrical characteristics, specifically its electrical impedance. When connected, the electrical drive signal from the system 100 goes to the transducer 200, and the acoustic output from the transducer 200 can be measured while at the same time, the electrical drive signal can be measured, so that the electro-acoustic efficiency of the transducer 200 can be evaluated.

The trigger circuit 346 samples the electrical drive signal and by comparing the drive signal to a threshold voltage, the start of the electrical drive signal can be determined. Since in many cases the electrical drive signal is pulsed, that is, has repeated sequences of being on and off, the trigger circuit 346 establishes when the signal has started. This trigger is then used to initiate the sampling of the electrical drive signal using the Analog-to-Digital Converter (ADC) 340. The timing circuit 344 uses the output from the trigger circuit 346 and the ADC clock 342 to control the action of the ADC 340. Alternatively, triggering may be provided in a different manner. For instance, the ADC 340 may run continuously using the ADC clock 342, and the trigger output may be used to indicate a specific time within the sample output stream from the ADC 340 that corresponds to the start of the pulse. While not shown in the diagram, the trigger circuit 346 can have an adjustable trigger threshold level, such level being controlled by a Control and Communication unit or controller 350. The controller 350 may be comprised of a microprocessor, a Field Programmable Gate Array (FPGA), Complex Programmable Logic Device (CPLD), etc. Controller 350 may control a Digital-to-Analog Converter (DAC) (not shown) that sets a voltage level for comparison with the electrical drive signal from the system 100. When the threshold level is exceeded, the ADC process is triggered. The electrical drive signal from the system 100 may be amplified by an amplifier or attenuated by an attenuator (not shown) before being sampled by the trigger circuit 346, such amplification or attenuation being digitally controlled by controller 350. The amplified or attenuated electrical drive signal is routed through a multiplexer 330 under the control of controller 350, so that the electrical drive signal can be sampled using the ADC 340.

The drive signal can be measured for amplitude, frequency, and pulse characteristics, such as pulse duration and the rate at which pulses occur (the pulse repetition interval). These data can be compared with the nominal setting of the system 100 to determine whether system 100 is operating as intended. The drive signal frequency can be determined from a fast Fourier transform (FFT) or other frequency measurement approach using software on the computer 500. The drive signal may be measured when connected to a known resistive load. For instance, a 50 Ohm load may be applied to the electrical drive signal from the system 100 to provide a reference condition.

When relay 310 isolates the transducer 200 from the system 100, the electrical impedance of the transducer 200 can be measured using the impedance measurement circuit 320. Impedance measurement circuit 320 operates at a frequency set by the frequency source 325, which is under the control of controller 350. The signal from the impedance measurement circuit 320 is routed through the multiplexer 330 to the ADC 340 at which it is sampled. The digital signal is passed through controller 350 to the computer 500 for analysis. The impedance measurement circuit 320 provides a drive signal to the transducer 200 and provides both this drive signal and the resultant current flow to the transducer 200 to the ADC 340. By using a dual ADC, such as Analog Devices AD9248, the amplitude and relative phase of the voltage and current can be used to determine the complex impedance of transducer 200 at any frequency as set by the frequency source 325. More specifically, the frequency source 325 can be set to the frequency of the drive signal as measured by the software on the computer 500. Thus, the electrical characteristics of the transducer 200 at the drive frequency can be established.

When relay 310 connects the transducer 200 to the system 100, the change in the drive signal can be observed, which is another indication of the condition of system 100. The transducer 200 may be acoustically coupled to the hydrophone assembly 400, and the ultrasound waveform output of the transducer 200 can be measured using the hydrophone element 450 within the hydrophone assembly 400, the output of which is sampled, via multiplexer 330, using the ADC 340. The multiplexer 330 allows for the same ADC 340 to be used for multiple measurements. However, another embodiment could have separate ADCs for each measurement need. Again, although not shown, the output from the hydrophone assembly 400 may be amplified or attenuated, as needed, by an amplifier or attenuator in order to boost the signal if it is too low or prevent signal saturation if it is too high. The attenuation or amplification may be provided under control of controller 350.

With the transducer 200 connected to the system 100, the drive impedance may be measured under load, and thereby provide another measurement data point of system integrity. This can be measured with a small series resistor interposed into the connection between system 100 and transducer 200 (not shown in FIG. 3).

Figure 4:
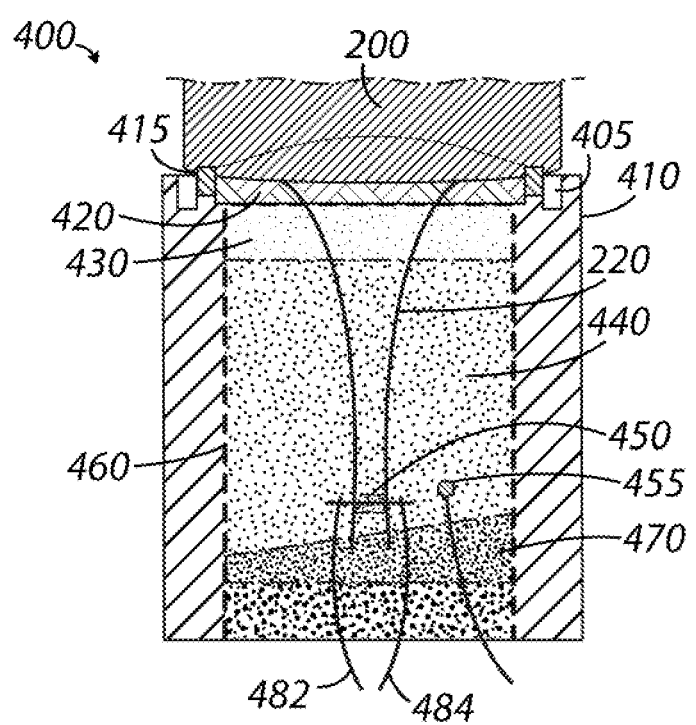
FIG. 4 is a schematic representation of a hydrophone assembly in accordance with embodiments of the invention.

FIG. 4 is a schematic representation of the hydrophone assembly 400. The schematic represents a cross section of the hydrophone assembly 400, which in the representative embodiment is a cylinder. The hydrophone assembly 400 has an outer casing or housing 410. The transducer 200 is shown sitting atop the housing 410. The top area of housing 410 has a matching element 415 that is designed to match and mate with a corresponding region of the front outer rim or face of transducer 200, so that when transducer 200 is placed on top of the hydrophone assembly 400 and received by the hydrophone assembly 400, the transducer 200 is centered collinearly with the central axis of hydrophone assembly 400, and the front face of transducer 200 is perpendicular to the central axis of hydrophone assembly 400. In that way, the central axis of ultrasound beam which is emitted from transducer 200 is aligned along the central axis of hydrophone assembly 400. The central axis of the ultrasound beam may be aligned by the matching element 415 to the center of the hydrophone element 450 to within less than one quarter or one eighth of the narrowest extent of the beam diameter. This eliminates the need for further mechanical alignment or positioning of the hydrophone element 450.

In order to acoustically couple the ultrasound energy from the ultrasound transducer 200 into the hydrophone assembly 400, a continuous mechanical conduction path is required. Due to the layers 430, 440 of solid materials included the hydrophone assembly 450, the continuous mechanical conduction path may be established with a small amount of water 420 placed in the top region of the hydrophone assembly 400 and over layer 430. The amount of water may be on the order of 20 cc, which is significantly smaller than a typical water tank for pressure measurements. Conventional tanks can contain tens of liters of water, which are heavy and inconvenient. The inner rim of the top region of housing 410 mates with the front of transducer 200 using a matching element 415 as noted earlier. When the transducer 200 is put in place and received by the matching element 415, some excess water may spill over the rim and be captured by a trough region 405 in the housing 410 adjacent to the matching element 415. The trough region 405 prevents water from spilling over the sides of the housing 410. Alternately, acoustic coupling gel may be used instead of water. Alternately, if the exact shape of the face of transducer 200 is known, a solid coupling material, similar to that used to create layer 440, may be created to form an exact inversion of the face of transducer 200. This solid coupling material would have the shape of the water 420 when transducer 200 is in place (i.e., received) on the transducer assembly 400, as shown in FIG. 4. In this case, only a very small amount of additional water or acoustic coupling gel would be needed to provide acoustic coupling.

The dashed lines 220 diagrammatically represent a typical focused ultrasound beam. The beam 220 has a focal region some distance from the face of the transducer 200, the focal region being the region where the beam is the narrowest, the amplitude is the highest, and the waves are traveling in a planar fashion. Ultrasound measurements are most repeatable in the region of the focus or beyond it, where the waves are planar. Measurements taken closer to the transducer than the focus can be highly variable because it is the so-called "near field" of the transducer; the "far field", at or beyond the focus, are much less variable in terms of spatial variability and especially phase uniformity. The hydrophone assembly 400 is configured to place a hydrophone, or ultrasound sensor, repeatably in the center of the ultrasound beam, at or beyond the focal distance. Depending upon their internal design, different transducers 200 can be focused at different focal depths. Those depths may not be known a priori, so an approach may be to position the hydrophone element 450 at a position deeper than any expected focal depth. This leads to a relatively tall hydrophone assembly 400.

In order to shorten this distance, the hydrophone assembly 400 includes an element or layer 430. Layer 430 is a disk or layer of a solid material with a different sound speed than the solid material of the subsequent layer 440, such that the ultrasound beam 220 is refocused to a shorter distance. This may reduce both the size and the cost of the hydrophone assembly 400. The layer 430 may have a convex or concave curvature, or a flat surface, at the interface to the subsequent layer 440. Depending upon whether a material is chosen with a higher or lower sound speed would drive whether the bottom surface is convex or concave, in order to provide a slight focusing lens. Suitable solid materials include polymers or plastics, such as Acrylic, which are relatively low attenuation but higher in sound speed (2,730 m/s for Acrylic) compared to the solid material of the layer 440. Such solid materials of the layer 440 may be machined to provide a smooth top surface facing the transducer 200, and also provide a leak-proof seal to contain water 420.

The subsequent layer 440 of the hydrophone assembly 400 is a solid material that permits the propagation of the ultrasound beam 220 with relatively little absorption or attenuation (scattering), and therefore is a substitute for water used in conventional hydrophone systems. The solid material of the layer 440 differs from the solid material of layer 430. Suitable solid materials may include low-durometer urethanes and low-durometer polyurethanes, with sound speeds from 1450 m/s to 1700 m/s. In an embodiment, the hardness of the low-durometer solid material of the layer 440 may range from 15 to 30 on a Shore A hardness scale. Another aspect of low-durometer urethanes is that they can be cast at room temperature. This allows the hydrophone element 450 to be positioned within the housing 410, and the coupling material of the layer 440 may be cast around it, fixing the hydrophone element 450 in place and embedding the hydrophone element 450. The hydrophone element 450 may be centered and positioned such that the direction of maximum sensitivity is aligned perpendicular to the axis of the ultrasound beam 220. For example, a disk-shaped hydrophone element would have the direction of maximum sensitivity perpendicular to the plane of the disk.

Beyond hydrophone element 450 (that is deeper and further along the propagation path of the ultrasound beam 220), the material and geometry may be chosen such that no or negligible reflection returns upward that would intersect the hydrophone element 450 from below and cause unwanted signal interference. Therefore, a layer 470 of sound-absorbing material may be cast behind layer 440. The solid material of the layer 470 differs from the solid material of the layer 430 and also differs from the solid material of the layer 440. The layer 470 of sound-absorbing material may be any of several solid materials, such as high-durometer urethanes, high-durometer polyurethanes, or high-durometer silicones. In an embodiment, the hardness of the high-durometer solid material of the layer 470 may range from 75 to 100 on a Shore A hardness scale. In an embodiment, the hardness of the high-durometer solid material of the layer 470 may be greater than the hardness of the low-durometer solid material of the layer 440. Acoustic scatterers, such as fine grain powders like tungsten, may be mixed into the material of the layer 470 to increase the ultrasound absorption of the material. The layer 440 in which the hydrophone element 450 is embedded and layer 470 of sound-absorbing material adjoin along an interface, and the interface between the layer 440 and the layer 470 may be angled with respect to the propagation direction of the ultrasound beam 220, in order to further minimize the chance of reflection. Other approaches, such as a mottled surface interface, may be used as well.

The layer 440 is positioned at least in part between the layer 470 and the hydrophone element 450. The layer 440 is also positioned at least in part between the layer 430 and the hydrophone element 450. Consequently, the propagation of the direction ultrasound beam 220 traverses the layer 430 and a portion of the layer 440 in order to reach the hydrophone element 450. The layer 430 is positioned between the matching element 415 and the hydrophone element 450. The layer 430, the layer 440, and the hydrophone element 450 are positioned between the matching element 415 and the layer 470. The layer 440 is positioned between the layer 430 and the layer 470 and may fully separate the layer 430 from the layer 470. The solid material of the layer 470 has a higher acoustic attenuation than the solid material of the layer 430 and also has a higher sound speed than the solid material of the layer 430.

A temperature-sensing element 455 may be positioned adjacent to the hydrophone element 450. The temperature-sensing element 455 may monitor the temperature of the material 440. If the transducer 200 creates excess heat while being driven by system 100, the excess heat could damage the hydrophone element 450 as well as the solid material in the layer 440. System 100 should be set to a level that does not create excess heat, but still has sufficient energy to provide a measurable signal on hydrophone element 450. Because this level may be unknown prior to testing, or may be accidentally exceeded, the temperature-sensing element 455 provides feedback that the system 100 should be shut down by the user or disconnected using the relay 310, in order to protect the hydrophone element 450. After shutdown or disconnection, the testing may be resumed after the temperature has dropped down to an acceptable level, and the output of the system 100 has been reduced. The output of the temperature-sensing element 455 may be connected to multiplexer 330 or may be measured by another type of instrument.

In an embodiment, the hydrophone element 450 may be comprised of any of a number of sensor materials. In an embodiment, the hydrophone element 45 may be comprised of a piezoelectric material, such as a piezoceramic, a piezoceramic composite, or a piezopolymer (e.g., polyvinylidene difluoride or PVDF, or co-polymers). In alternative embodiments, the hydrophone element 450 may be a different type of device, such as an electromagnetic sensor or a capacitive sensor. Piezopolymers may be acoustically transparent so as not to disturb the ultrasound field and cause reflections, and generally have a broad bandwidth so that they respond to a range of frequencies. Piezoceramics generally produce higher output voltages for a given pressure amplitude than piezopolymers. In an embodiment, the sensor material of the hydrophone element 450 may be chosen to respond to a mechanical pressure applied by the ultrasound beam 220 by generating an electric charge in accordance with the piezoelectric effect.

The physical size of the hydrophone element 450 may be matched to the expected width of the focal zone and the ultrasound beam 220. The smaller the size, the lower the sensitivity of the hydrophone (voltage out compared to pressure exposure). The smaller size may also increase the requirement for proper physical alignment of the transducer 200 on the top of the hydrophone assembly 400. However, too large a hydrophone aperture may lead to spatial averaging of the beam, which can also cause unwanted signal instability during measurements. In an embodiment, the hydrophone element 450 is a circular disk shape, and the diameter of the hydrophone element 450 is on the order of the expected diameter of the ultrasound beam 220. Other hydrophone configurations, such as small rings or cylinders, are possible as well. The system may also be modified to include multiple hydrophone elements, allowing for a measurement of the beam width properties. A multiple hydrophone element system may require additional multiplexer input connections with potentially multiple preamplifiers, etc., as needed.

Thus, the design of the hydrophone assembly 400 is matched to the design of the transducer 200 and the shape of the ultrasound beam 220. Both the depth and the width of the ultrasound beam 220 are taken into consideration. The focal depth sets the distance to the hydrophone element 450, taking into account the refocusing layer 430, if it is used. The focal width sets the diameter of the hydrophone element 450, such that the majority of the main lobe of the ultrasound beam 220 is captured by the hydrophone element 450, but any side lobes (which are generally out of phase with the main lobe) are not captured. The hydrophone element 450 should be in the far field region of the ultrasound beam 220, such that the waves are planar.

The electrical connections from the hydrophone element 450 are shown as wires 482 and 484. These emerge from the rear of layer 470, and are then connected to the circuit that comprises the remainder of the electronics module 300. An amplification stage may be inserted between the hydrophone element 450 and the multiplexer 330, or in the case of designs in which there are multiple ADCs, an amplification stage may be inserted between the hydrophone element 450 and the ADC. The amplification stage may be variable, with the gain changing to meet the requirements of adequate signal to noise ratio (SNR) and sensitivity at the input of the ADC 340.

Layer 470 shown in FIG. 4 may provide electrical shielding that is used to prevent the pickup of extraneous electrical interference by the hydrophone element 450. The hydrophone element 450 may be susceptible to low frequency (60 and 120 Hz) power line signals, as well as higher frequency signals at the drive frequency of the transducer 200, and high frequency electromagnetic signals from nearby electronic equipment such as MM machines, computers, etc. In an embodiment, the signal wires 482 and 484 continue to the electronics module 300 as a shielded twisted pair, with the shielding in electrical continuity with the shield provided by the layer 470, thus completely shielding the hydrophone element 450 from interference. This can significantly improve the signal-to-noise ratio (SNR) of the system.

The hydrophone assembly 400 may be located remotely from the electronics module 300. This may be necessary in the cases where the transducer 200 is located remotely from the system 100, for instance, in the case wherein the transducer 200 is in the room with an MM system. This is noted by the vertical dashed line in FIG. 2, with the MRI room noted on the right hand side of the line. In such cases, there is a strong magnetic field present in the room, even when the MRI is not active. In that circumstance, electronic components within the electronics module 300 may negatively interact with the static magnetic field. The hydrophone assembly 400, which consists mostly of plastic and polymer materials, is unaffected by the magnetic fields. A suitable preamplifier (or preamplifiers, in the case of multiple hydrophone elements) may be located with hydrophone assembly 400 in order to transmit the signal from the hydrophone element 450 to the electronics module 300, which would be located outside of the MRI room.

Figure 5:
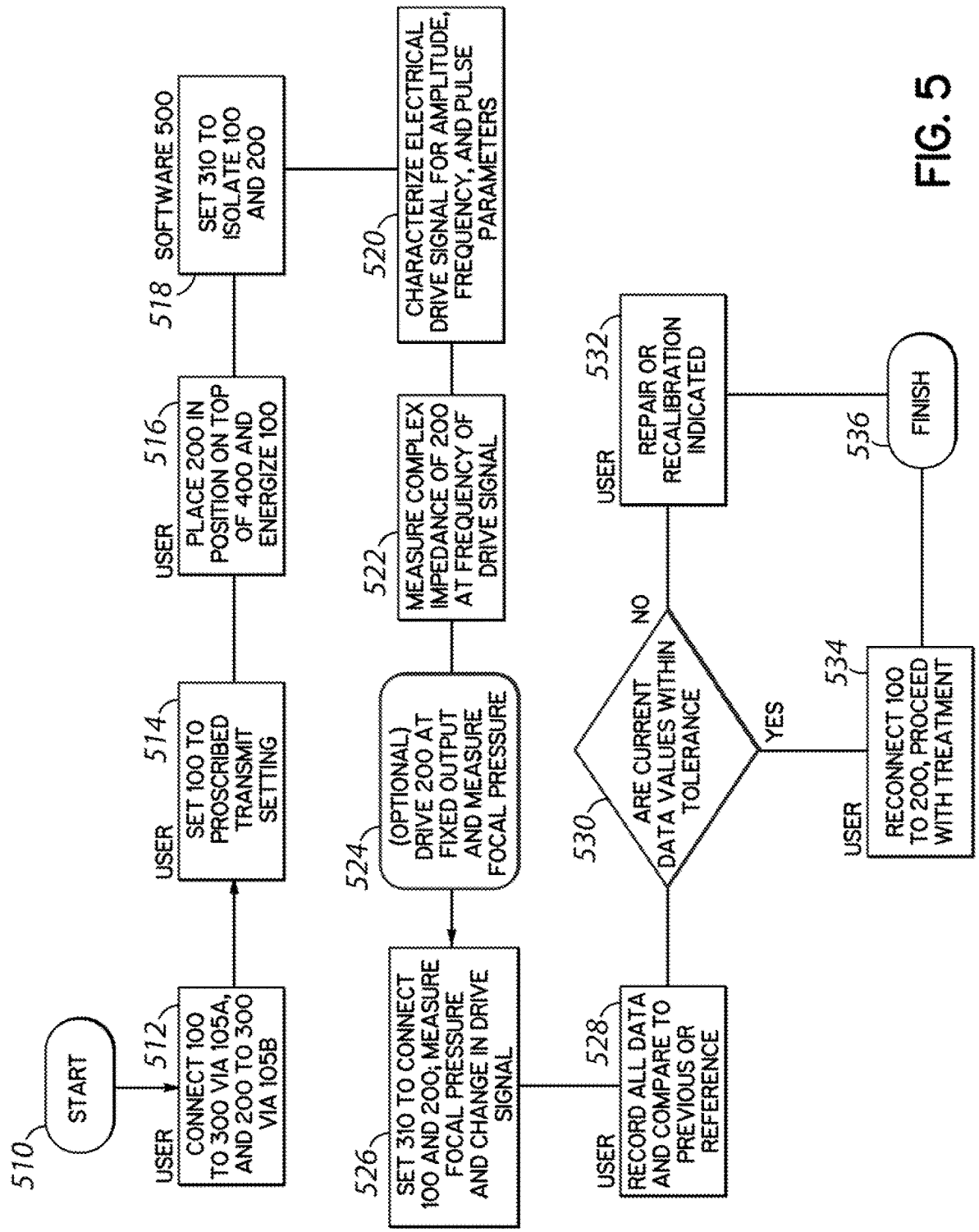
FIG. 5 is a flow chart showing operation of the system of FIG. 2 in accordance with embodiments of the invention.

FIG. 5 is a flow chart illustrating the operation of the system 100 in accordance with embodiments of the invention. The process begins with the user connecting the system 100 to electronics module 300 via connector 105A and connecting the transducer 200 to the electronics module 300 via connector 105B (block 512). Note in the flow chart, blocks 512, 514, 516, 528, 532, and 534 may be conducted by the user, while the other blocks may be run under software control of the computer system 500, although not so limited.

In block 514, the user sets the system 100 to a proscribed output condition, so that the measurement to be taken at that time and all future measurements are conducted under nominally identical conditions. The system 100 may be set to a convenient combination of drive voltage, pulse duration, and pulse repetition interval such that resulting drive waveform results in a high-fidelity measurement.

The output of system 100 should not be so high as to cause undue heating of the hydrophone assembly 400, nor so low as to incur signal to noise issues with the hydrophone element 450. The pulse duration should be long enough for good signal-to-noise ratio, but short enough such that the ultrasound signal received at the hydrophone element 450 is temporally separated from the time of the electrical drive signal. This may be relevant if the transducer 200 is not sufficiently electrically shielded, although the entire hydrophone assembly 400 does include shielding 460 to prevent or minimized electrical interference. For example, if the acoustic propagation time from transducer 200, through water 420, layer 430, and layer 440 to hydrophone element 450 is 40 microseconds, then the pulse duration should be less than 40 microseconds. The propagation time will be a function of the sound speed of the intervening water 420, layer 430, and layer 400, and the distance of sound travel through each of the water 420, the layer 430, and the layer 400. If transducer 200 is adequately shielded, it will not be necessary to "time separate" the drive from the sensed acoustic signal.

In block 516, the user places transducer 200 in position on the top of hydrophone assembly 400, making sure that the water 420 makes complete contact with the transducer face, spilling over slightly into trough region 405, and that transducer 200 is centered and aligned. The design of the top of the housing 410 is such that it is a physical match to the front of transducer 200. Different transducers may have different front face designs. Therefore, interchangeable top sections of housing 410 may be needed to fit different transducer designs, including circular, rectangular, oblong, etc. Once the transducer 200 is correctly positioned on the top of housing 410, the user energizes system 100 to produce electrical drive signals.

In block 518, under software control of computer 500 interfaced to controller 350 within electronics module 300, relay 310 is set to isolate system 100 from transducer 200. System 100 may be connected to a fixed resistive load for test purposes.

In block 520, the electrical drive signal from system 100 is analyzed for characteristics such as but not limited to voltage amplitude, frequency, bandwidth, pulse duration, pulse repetition frequency, average power, etc. The analysis is done by analog-to-digital conversion and waveform sampling, data transfer to computer 500, and data analysis by the program running on computer 500. Alternative analysis devices, including RMS to voltage converters (such as Analog Devices AD8436 or AD636), peak detector circuits, filters, etc., may be used. The analysis may be done directly on the sampled signal, or it may be down-converted to a lower baseband frequency range.

In block 522, the electrical impedance characteristics of transducer 200 are measured, specifically informed by knowing the frequency of drive signal based on the analysis of block 520. The complex impedance of transducer 200 may be determined by driving with a fixed voltage signal at the specific frequency from element 320, detecting the current, and simultaneously measuring the voltage and current signals to determine amplitude and phase relationships. The dedicated impedance hardware, element 320, computes the current based on measuring the voltage drop across a high side source resistor. Changes in transducer complex impedance can indicate issues such as connection failures, cracking of the piezoceramic element, internal delamination, etc. The impedance measurement may also be conducted over a range of frequencies.

In block 524, the transducer 200 is driven at the specified frequency (or other frequencies) from circuits within electronics module 300 (not shown in FIG. 3) while measuring the signal from the hydrophone element 450. In an embodiment, the electronics module 300 is powered from the USB connection to the PC 500 and there may not be sufficient power to drive transducer 200 such that an acoustic signal is measured by hydrophone element 450. However, other arrangements may be used to supply power to electronics module 300 separately and at sufficient levels that a representative drive signal is provided to the transducer 200. If a drive signal is provided from electronics module 300, it provides an independent, repeatable measurement condition to assess the function and condition of the transducer 200.

In block 526, the software, via the connection to the computer and controller 350, changes the state of relay 310 such that system 100 and transducer 200 are connected. The change in the drive voltage that occurred as the load was switched from a purely resistive load (block 520) to the actual load of transducer 200, provides an indication of the condition of the drive electronics of the system 100. The impedance measurement of the drive active may be done by measuring the current waveform in a sense resistor. The output of the transducer 200 is measured using hydrophone element 450, and an estimate of the electro-acoustic efficiency of transducer 200 can be made. In addition, the change in the output of transducer 200 over time can be monitored by regular use of this method.

In block 528, the data gathered by the various measurements just described are recorded. This recordation can either be manually by the user or automatically by the software running on computer 500.

In block 530, the data is compared with prior measurements, and evaluated as to whether there has been a change of more than a set amount, or a percentage change from prior values or some reference value. If the values are within specification, then the user connects system 100 to transducer 200 and proceeds treatment of tissue (step 534). If the values are out of specification, then the transducer 200 or system 100 are considered suspect and should not be used without further investigation, and potentially recalibration or repair (step 532).

The embodiments of the invention incorporate both electrical and acoustical testing within a single device, and done so in a manner that is convenient to a non-technical user, in a clinical environment.

The embodiments of the invention automatically evaluate the system 100 and transducer 200 both independently and in concert, electrically and acoustically.

The embodiments of the invention provide for a hydrophone assembly 400 in a measurement system that uses a minimum of water. Rather than a tank of water, the hydrophone element 450 is embedded in a castable layer 440 of the material which provide an acoustic pathway of solid material. Embedment in a solid material significantly improves the stability of the positioning of the hydrophone element 450. The mating of transducer 200 to the housing 410 provides for a precision alignment of the ultrasound beam 220 and the hydrophone element 450.

The small amount of coupling water at the top of housing 410 is significantly less than other water-tank-based hydrophone measurement systems. The overflow trough approach (i.e., trough region 405) minimizes the chance of a water spill in a clinical environment while at the same time ensuring complete acoustic coupling of the transducer 200 to the measurement system provided by the hydrophone assembly 400.

The hydrophone element 450 may be consistently positioned in the far field of the ultrasound beam 220, where the pressure waveform is planar and in phase.

Layer 430 may be used to foreshorten the focal depth and reduce the overall length of the hydrophone assembly 400, and this is controllable by the selection of the material, the sound speed of the material, the material thickness, and the radius of curvature of the convex or concave bottom surface of the layer 430.

Layer 440 provides a water equivalent medium which is a solid material and can contain the hydrophone element 450 as an embedded element. By casting this material, it can be more conveniently constructed with minimal cost.

Hydrophone element 450 is a small sensor of the appropriate piezoelectric material, in a planar or other appropriate shape, which provides an electrical signal proportional to the pressure in the ultrasound beam 220.

Example

A hydrophone embedded in a solid material was used as a receiver. The hydrophone was tested using a 61 mm diameter, 80 mm focal length transducer, driven with a $20V_{p-p}$, 650 kHz, pulsed waveform. Hydrophone elements made from PVDF, piezo-copolymer, and ceramic were tested with output voltages between 0.5 and $3V_{p-p}$ using a high impedance, low capacitance input. The sensors were demonstrated to be stable over time with less than 2% difference in output.

Figure 6:
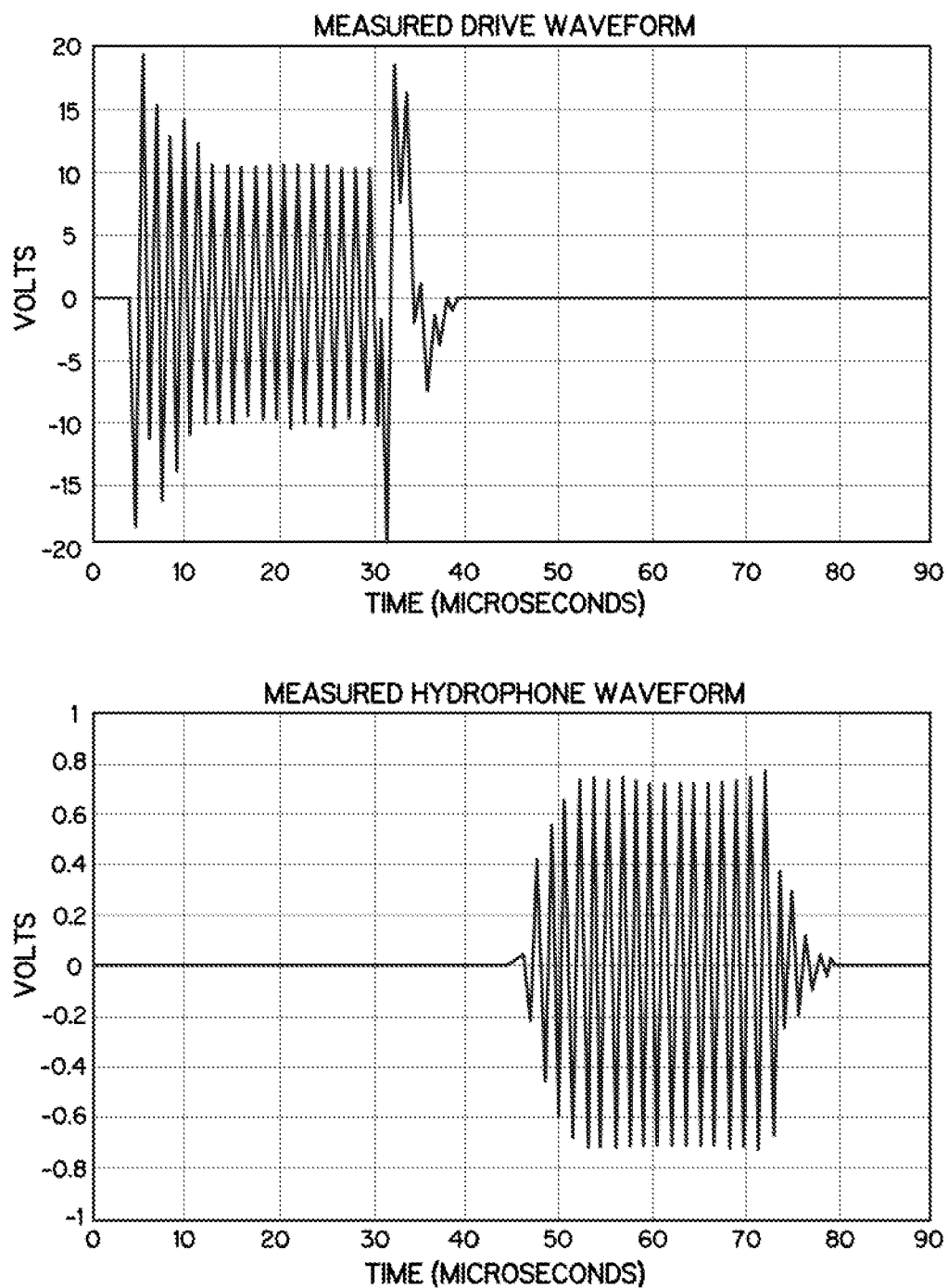
FIG. 6 is an example of results from testing.

FIG. 6 is an example of results from such a test. The upper waveform is a measurement of the drive waveform to the 61 mm, 80 mm focal length transducer, showing the $20V_{p-p}$, 650 kHz pulsed waveform. As is typical when driving a capacitive load such as a piezoelectric element, there are voltage overshoots at the beginning and end of the pulse.

The lower waveform in FIG. 6 is the measurement of the received waveform from a PVDF sensor with a 5 mm active diameter, embedded in a cast urethane cylinder, with a construction design as shown in FIG. 4. The received waveform has an amplitude of about $1.5V_{p-p}$, at a time offset (delay) from the transmit pulse that corresponds to the time taken for the ultrasound wave to travel through the urethane from the transmit transducer to the receiver. This demonstrates that the signal can be received with good signal-tonoise ratio, at an amplitude that is sufficient for Analog to Digital conversion and further signal analysis, and that has good signal fidelity.

The embodiments of the invention may provide a single system that tests both the therapeutic ultrasound system electronics and transducer, separately and together, and provides a specific metric (pressure waveform data) which is directly related to treatment efficacy.

The embodiments of the invention may provide a measurement system and method that can be used by non-technical personnel in a clinical environment and provide a quantitative metric that can be easily tracked over time.

The embodiments of the invention may provide a measurement system that requires very little water to couple the ultrasound transducer to the measurement system.

The embodiments of the invention may provide a convenient interconnection method that can be used by non-technical users.

The embodiments of the invention may provide a computerized method that guides the user through a simple flow of a relatively sophisticated measurement process in which the process is automated through the use of internal relay connection and disconnection of the ultrasound drive electronics and transducer.

The embodiments of the invention may provide a test device placed in between the ultrasound drive electronics and transducer, which can test both elements independently, can test the functioning of the system as a whole, and appraise the effects of the transducer on the drive electronics.

The embodiments of the invention provide frequency analysis of the drive waveform to determine the frequency at which to make complex impedance measurements of the transducer.

The embodiments of the invention may provide the combination of measuring the electrical drive, the acoustic output, and impedance in the same instrument.

The embodiments of the invention may provide a broad range of measurements and evaluation techniques to determine that the therapeutic ultrasound system under test is operating correctly.

The embodiments of the invention may provide a hydrophone embedded in specific materials, at specific depths, obviating the need for a large water tank.

The embodiments of the invention may provide a hydrophone measurement system that provides signal acoustic signal fidelity without requiring water around the hydrophone element.

The embodiments of the invention may provide a hydrophone measurement system that shortens the physical distance required between the transducer and the hydrophone element by including a secondary focusing element (i.e., layer 430).

The embodiments of the invention may provide a hydrophone measurement system that positions the hydrophone in the far field of the ultrasound beam where plane wave propagation predominates for improved signal fidelity.

The embodiments of the invention may provide a hydrophone measurement system that has a hydrophone active receiving area that is sized to capture the main lobe of the ultrasound beam and not any of the side lobes for improved signal fidelity and stability.

The embodiments of the invention may provide peak pressure, average intensity, and pulse characteristics of an ultrasound transducer in its working environment, just prior to or just after a treatment session.

The embodiments of the invention may provide peak voltage, average power, and pulse characteristics of an ultrasound drive system in its working environment, both in an isolated condition and while driving an ultrasound transducer.

The embodiments of the invention may permit the position of the transmitting transducer to be locked or fixed relative to the hydrophone, such that no scanning or hydrophone positioning is required, and the same measurement conditions (geometry of the transducer and hydrophone) can be repeated, allowing for consistency checks over time.

In certain alternative embodiments, the functions, acts, and/or operations specified in the flowcharts, sequence diagrams, and/or block diagrams may be re-ordered, processed serially, and/or processed concurrently consistent with embodiments of the invention. Moreover, any of the flowcharts, sequence diagrams, and/or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising".

While all of the invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. An apparatus for calibrating an ultrasound transducer, the apparatus comprising:
    a hydrophone assembly including a first layer comprising a first solid material, a second layer comprising a second solid material different from the first solid material, a matching element configured to receive the ultrasound transducer, and a hydrophone element embedded in the first solid material of the first layer, the first layer positioned at least in part between the second layer and the hydrophone element, and the first layer and the hydrophone element positioned between the matching element and the second layer.

2. The apparatus of claim 1 wherein the hydrophone element comprises a piezoelectric material.

3. The apparatus of claim 1 wherein the first solid material comprises a low-durometer urethane or a low-durometer polyurethane.

4. The apparatus of claim 1 wherein the second layer is positioned between the matching element and the hydrophone element.

5. The apparatus of claim 1 wherein the first solid material comprises a low-durometer urethane or a low-durometer polyurethane, and the second solid material comprises an acrylic.

6. The apparatus of claim 1 wherein the first solid material comprises a low-durometer urethane or a low-durometer polyurethane, and the second solid material comprises a high-durometer urethane, a high-durometer polyurethane, or a high-durometer silicone.

7. The apparatus of claim 1 wherein the first layer and the second layer adjoin along an interface, and the interface is angled with respect to a propagation direction of an ultrasound beam from the ultrasound transducer.

8. The apparatus of claim 7 wherein the second solid material has a higher acoustic attenuation than the first solid material.

9. The apparatus of claim 7 wherein the second solid material has a higher sound speed than the first solid material.

10. An apparatus for calibrating an ultrasound transducer, the apparatus comprising:
a hydrophone assembly including a first layer comprising a first solid material, a second layer comprising a second solid material different from the first solid material, a matching element configured to receive the ultrasound transducer, and a hydrophone element embedded in the first solid material of the first layer, the first layer positioned at least in part between the second layer and the hydrophone element,
wherein the hydrophone assembly includes a third layer comprising a third solid material different from the first solid material and the second solid material, and the first layer and the hydrophone element are positioned between the second layer and the third layer.

11. The apparatus of claim 10 wherein the first solid material comprises a low-durometer urethane or a low-durometer polyurethane, the second solid material comprises an acrylic, and the third solid material comprises a high-durometer urethane, a high-durometer polyurethane, or a high-durometer silicone.

12. The apparatus of claim 1 wherein the matching element is configured to align a central axis of an ultrasound beam emitted from the ultrasound transducer with a center of a face of the hydrophone element.

13. The apparatus of claim 12 wherein the hydrophone assembly includes a housing, and the housing includes a trough region that extends about the matching element.

14. The apparatus of claim 1 wherein the hydrophone assembly further includes a temperature sensing element positioned in the first layer adjacent to the hydrophone element.

15. The apparatus of claim 10 wherein the hydrophone assembly further includes a temperature sensing element positioned in the first layer adjacent to the hydrophone element.

16. The apparatus of claim 1 wherein the hydrophone assembly includes a housing, and the housing includes a trough region that extends about the matching element.

17. The apparatus of claim 1 wherein the hydrophone assembly includes a third layer comprising a third solid material different from the first solid material and the second solid material, and the first layer and the hydrophone element are positioned between the second layer and the third layer.

18. The apparatus of claim 10 wherein the first solid material comprises a low-durometer urethane or a low-durometer polyurethane.

19. The apparatus of claim 14 wherein the first solid material comprises a low-durometer urethane or a low-durometer polyurethane.

* * * * *